(12) United States Patent
Herrmann et al.

(10) Patent No.: US 7,337,074 B2
(45) Date of Patent: Feb. 26, 2008

(54) METHOD AND APPARATUS FOR DETERMINING THE MASS OF PORTIONED UNITS OF ACTIVE SUBSTANCES

(76) Inventors: Rainer Herrmann, Kottwitzstrasse 15, Hamburg (DE) 20253; Stefan Zaage, Schierholzstr 25c, Hannover (DE) 30655; Udo Schlemm, Weidenstieg 10, Hamburg (DE) 20259

( * ) Notice: Subject to any disclaimer, the term of this patent is extended or adjusted under 35 U.S.C. 154(b) by 98 days.

(21) Appl. No.: 10/820,244

(22) Filed: Apr. 6, 2004

(65) Prior Publication Data

US 2004/0225454 A1    Nov. 11, 2004

(30) Foreign Application Priority Data

Apr. 8, 2003    (EP) .................................. 03008198

(51) Int. Cl.
*G01N 31/00* (2006.01)
(52) U.S. Cl. ...................................................... 702/23
(58) Field of Classification Search ................ 702/23, 702/26, 75, 128, 129; 324/633, 637
See application file for complete search history.

(56) References Cited

U.S. PATENT DOCUMENTS

| | | | |
|---|---|---|---|
| 3,841,836 A * | 10/1974 | Lunsford et al. ............ 422/134 |
| 5,515,740 A | 5/1996 | Gamberini ................. 73/865.8 |
| 5,554,935 A | 9/1996 | Kraszewski et al. ......... 324/663 |
| 5,602,485 A | 2/1997 | Oestreich et al. ........... 324/663 |
| 5,977,780 A * | 11/1999 | Herrmann ..................... 324/640 |
| 6,630,563 B2 * | 10/2003 | Hucks et al. ................ 528/196 |
| 6,837,122 B2 * | 1/2005 | Herrmann et al. ............ 73/865 |
| 6,897,659 B2 * | 5/2005 | Herrmann et al. .......... 324/633 |
| 6,906,164 B2 * | 6/2005 | DeBruin .................. 528/308.1 |
| 6,922,061 B2 * | 7/2005 | Herrmann et al. .......... 324/633 |
| 7,211,633 B2 * | 5/2007 | DeBruin ....................... 526/64 |
| 2002/0139264 A1 | 10/2002 | Bartscher et al. ........... 101/232 |
| 2004/0017207 A1 * | 1/2004 | Herrmann et al. .......... 324/633 |
| 2005/0054814 A1 * | 3/2005 | DeBruin .................. 528/308.1 |
| 2005/0096202 A1 * | 5/2005 | Teufel et al. ................. 493/39 |

FOREIGN PATENT DOCUMENTS

| | | | |
|---|---|---|---|
| DE | 40 04 119 A | | 8/1991 |
| DE | 201 19 344 U1 | | 4/2003 |
| EP | 1 327 876 | * | 7/2003 |
| EP | 1 467 191 | * | 10/2004 |
| JP | 63-045547 | * | 2/1988 |
| JP | 63-210757 | * | 9/1988 |

OTHER PUBLICATIONS

No. XP-002252639—Contactless Mass Determination of Arbitrarily Shaped Objects by Microwave Resonator Measurements, 1994.

* cited by examiner

*Primary Examiner*—Michael Nghiem (57) ABSTRACT

A method and the apparatus for determining the mass of portioned units of active substances, in particular capsules, tablets or dragees, involves leading the units of active substances through a microwave resonator and determining the mass from the displacement of the resonant frequency and the broadening of the resonance curve.

12 Claims, 8 Drawing Sheets

METHOD AND APPARATUS FOR DETERMINING THE MASS OF PORTIONED UNITS OF ACTIVE SUBSTANCES

BACKGROUND OF THE INVENTION

The invention relates to a method and an apparatus for determining the mass of portioned units of active substances, in particular capsules, tablets or dragees, in particular in the pharmaceutical industry.

In the case of portioned units of active substances, it is important to monitor whether each unit of active substances actually has the desired mass. As a result, it is possible for example to determine whether a casing has been filled incompletely or not at all. A customer would rightly be dissatisfied if the units of active substances acquired by him did not contain the quantity of active substances which he expected. This applies in particular to the pharmaceutical sector, where accurate metering of the units of active substances matters.

In the pharmaceutical industry, the pharmaceutical active substances, together with specific filler substances such as starch, lactose and so on, are pressed in tablet form by specific filling machines or put into gelatin-like capsules or formed as dragees. The corresponding machines reach high production speeds with filling rates of less than 50 000 to more than 300 000 per hour. It is critical to the effectiveness of the pharmaceutical preparation that the unit of active substances contains the necessary quantity of active substances and this is also actually maintained at the high filling rates. The volume contents of the units of active substances in the pharmaceutical sector vary between 800 mg in the case of large capsules down to 50 mg or, in the case of very small doses, down to 5 mg.

It is known to determine or to monitor the masses of the units of active substances produced by means of weighing (DE 198 19 395 C1). Because of the large number of units of active substances per unit time, and on account of the fact that the mechanical weighing operation naturally needs a certain amount of time, it is possible either only for random samples to be removed and weighed and/or it is necessary for a large number of devices arranged in parallel to be provided for the weighing. Using random samples, however, only the general quality of the units of active substances produced can be checked. Individual checking is not possible, and so deviations of individual samples from the average quality cannot be monitored and removed. On the other hand, the weighing of each individual unit of active substances by means of weighing devices arranged in parallel is very complicated. Even if, for example, 20 weighing devices were to be used, at the rates specified above, each weighing device would still have to weigh 15 000 units of active substances per hour, that is to say around 4 per second, which still signifies great technical difficulties. The individual units of active substances have to be stopped mechanically on the weighed goods receiver at these production speeds and accelerated beforehand and afterwards. The jolting and abrupt movements lead to considerable mechanical stressing of the units of active substances. Furthermore, in particular in the case of units of active substances provided with casings and with small filling masses, the disadvantage arises that the statistical fluctuations of the mass of the casing are reflected completely as measurement errors of the filled weight. A separate, twofold weighing of the same unit of active substances with and without filling could rule out this error, but, in the case of weighing technology being used, this increases the problems still further. In addition, as a result of the sensitive mechanical guidance in these balances, if there were a change in the format of the units of active substances to be weighed, considerable mechanical conversion of product guides would be necessary.

Attempts have also been made to overcome the above disadvantages, which are brought about by the inertia of the weighing technology, by means of capacitive measuring techniques (U.S. Pat. No. 4,223,751 A, U.S. Pat. No. 5,602, 485 A, DE-A 29 39 406). With this method, with units of active substances moved at high speed through the capacitor, a mass-proportional electric signal can be determined only if the moisture content of the units of active substances and of the filler material remains exactly constant. As a result of slight fluctuations of the water content of the active substance in the units of active substances, because of the high dielectric constant of the water, a disproportionate change in the mass signal is produced. A small change in the moisture thus produces a large deviation in the mass signal from the actual mass.

An object of the invention is to provide a method and an apparatus of the type mentioned at the beginning with which the mass of the units of active substances can be determined reliably, accurately and quickly without excessive expenditure.

SUMMARY OF THE INVENTION

One solution according to the invention is a method for determining the mass of portioned units of active substances, in particular capsules, tablets or dragees, in which the units of active substances are led through a microwave resonator and, from the displacement A of the resonant frequency and the broadening B of the resonance curve, the mass M is determined, with compensation of the influence of the moisture, by means of a mathematical combination of the two measured variables, which employs a linear expansion of M with respect to A, each of the coefficients representing a linear expansion with respect to F, where $F=B/A$.

Although it is known to determine the mass of particles with the aid of microwaves (U.S. Pat. No. 5,554,935 A), these are plastic particles, in which moisture problems do not occur and the moisture does not have to be taken into account. Therefore, the measurement of the moisture also plays only a subordinate role there. This method can therefore not be used generally for measuring units of active substances. In addition, in the case of the previously disclosed method, it is not the change in the width of the resonance curve but the change in the transmission coefficient which is measured. In this case, the transmission amplitude can be determined substantially less accurately and less reproducibly by measurement than the width of the resonance curve. Influencing variables on the transmission amplitude are the temperature and the aging of the components of the measuring electronics. In addition, the transmission amplitude is influenced by cable resonances which occur, while the width of the resonance curve is independent of such influences.

However, the invention not only differs from the prior art as a result, but also permits a particularly simple determination with the aid of a simple linear expansion of the mass as a function of the displacement of the resonant frequency. This is carried out while compensating for the influence of moisture.

In this case, the invention can make use of a method with which the mass and/or the moisture of a material can be determined (EP 0 468 023 B1). It is the contribution of the invention to have found that the principle of measurement with microwaves can also be used for determining the mass of portioned units of active substances. The measurement with microwaves has the advantage that it is very quick. The displacement of the resonant frequency or the width of the resonance curve will change correspondingly quickly when particles are led through the microwave resonator. The invention has recognized the fact here that the signal generated can be evaluated in such a way that the mass of the individual units of active substances can nevertheless be determined. This is done, for example, by determining in each case the maximum of the displacement of the resonant frequency and/or the width of the resonance curve during the passage of a unit of active substances.

The aforementioned known method (EP 0 468 023 B1) and similar known methods permit the simultaneous measurement of two properties of the dielectric product which is currently located in the measuring field of the resonator:

1. The change A in the resonant frequency as compared with the resonant frequency of the empty state, an effect which is proportional to the dielectric constant (real part) of the unit of active substances and therefore its mass.
2. The increase B in the half-value width of the resonance curve as compared with that of the empty state, an effect which is not only proportional to the mass of the unit of active substances but also to the conversion of microwave energy into heat by the water contained in the product (imaginary part of the dielectric constant).

The invention has recognized that this previously known method permits the determination of the mass in a particularly simple and direct way while compensating for the moisture. In this case, in addition to or instead of the moisture compensation, a determination and possible display of the moisture can also be carried out, in order in this way to be able to determine quality fluctuations better.

A particularly advantageous and simple embodiment is distinguished by the fact that the mass is determined with the aid of the relationship $$M = k1 * (1 + k2 * F) * A$$

where k1 and k2 are constants, of which k2 depends on the unit of active substances examined and F=B/A.

During the determination of the mass of portioned units of active substances which comprise a casing and the active substance contained therein, provision can be made in an advantageous embodiment for the mass of the casing without active substance and then the total mass of the unit of active substances following filling with the active substance to be determined. As a result, it is possible to ensure that, even when there is a nonuniform mass of the casings, the same quantity of active substance is always contained in the casings.

Provision could be made for the empty casings to be sorted by mass and then to be filled batchwise with the same mass and for the total mass to be determined. However, it is more expedient if the mass of the casing is determined immediately before filling. The individual units of active substances, whose speed is known, can then be tracked electronically from the first measurement point to the second measurement point, so that the empty weight and the filled weight of each individual unit of active substances can be correlated with each other.

The measurements are expediently carried out at microwave frequencies from 1 to 60 GHz, in particular 2 to 30 GHz.

If, with the method, a deviation of the mass of active substance from a predefined tolerance band is determined, then the active substance capsule can be removed by methods known per se, such as a mechanical diverter or puff of air.

A further achievement of the object involves providing an apparatus for determining the mass of portioned units of active substances, in particular capsules, tablets or dragees, which comprises a microwave generator, a microwave resonator, a device for guiding the unit of active substances through the microwave resonator, measuring and evaluation electronics for determining the mass from the displacement A of the resonant frequency and the broadening B of the resonance curve, and a device for removing individual units of active substances.

The devices for guiding the units of active substances can have a tube, through which the units of active substances are conveyed by an air stream. On the other hand, provision can be made for an endless belt with depressions to be provided, into which the units of active substances are inserted and which is moved through the resonator.

A further advantageous alternative consists in a circular disk, on the circumference of which the units of active substances are held firmly with the aid of vacuum. Following the measuring operation, the particles can then be removed quickly from the disk by a slight positive pressure.

If use is made of a carrier in the form of an endless belt or a disk, then its mass contributes to the displacement and broadening of the resonance curve. This contribution must be determined in advance. If the belt or the disk is not completely uniform, in this case the irregularities must be correlated with the location on the belt or the disk, so that different corrections are made for different units of active substances. Alternatively or additionally, this mass contribution can however also be measured between individual units of active substances at the point where there is no unit of active substances. This opens up the possibility of determining and compensating for gradual changes arising, for example, from contamination or temperature changes.

An expedient apparatus for determining the mass of units of active substances which comprises a casing and the active substance contained therein is distinguished by the fact that it has a second microwave resonator with measuring and evaluation electronics for determining the mass of the units of active substances before filling.

BRIEF DESCRIPTION OF THE DRAWINGS

The invention will be described by way of example in the following text using advantageous embodiments and with reference to the appended drawings, in which.

DETAILED DESCRIPTION OF THE PREFERRED EMBODIMENTS

Figure 1:
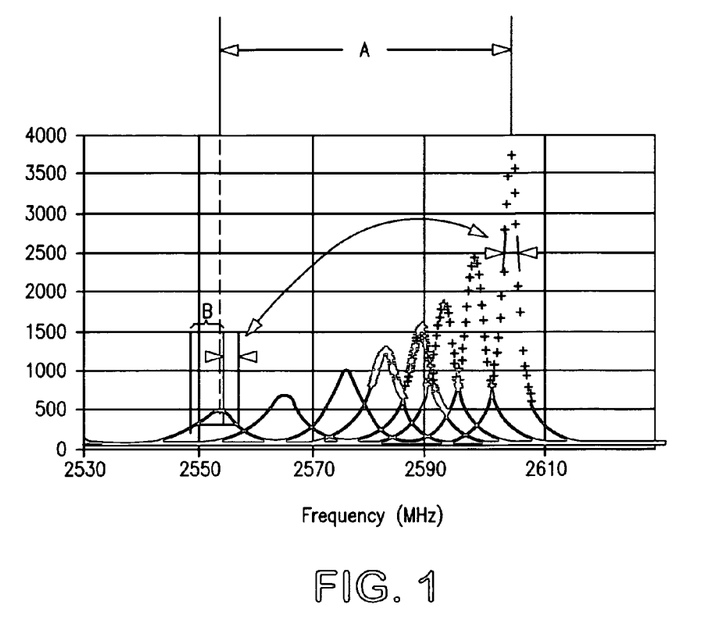
FIG. 1 shows the influence of different capsule sizes usual in the pharmaceutical industry on the displacement of the resonant frequency and the broadening of the resonance curve of a microwave resonator.

The effect on the microwave resonance of the different capsule sizes usual in the pharmaceutical industry is shown by FIG. 1. The greater the mass of the capsule, the greater is the displacement A of the resonant frequency as compared with the resonant curve of the empty resonator, arranged on the far right. The greater also are the attenuation and broadening B of the resonance curve brought about by the water contained in the powder of the capsule. The ratio of the two variables, F=B/A, is substantially independent of the mass of the capsule and is a measure of the percentage proportion of the water. The invention has recognized that expressions of higher order which exist in theory can be disregarded. Of course, this also applies to tablets, dragees or other units of active substances. Therefore, the resonator method not only provides a measured variable A (or B) proportional to mass for determining the mass but also a variable F for determining moisture and at the same time for compensating for the influence of moisture on the mass signal. A simple but effective method comprises, for example, in calibrating the mass M of the unit of active substances with respect to a direct mass measurement with a balance at two different moistures, and therefore determining the coefficients k1 and k2 of the following equation:

$$M=k1*(1+k2*F)*A$$

As a rule, k2 is a typical constant for the relevant unit of active substances and can be stored in the memory of the CPU of the filling machine and called up under the appropriate keyword for the filler material (for example of starch or lactose and so on). For simple quick calibration, the determination of the constant k1 as a single-point calibration is then sufficient. This can even be done online since monitoring in the manner of random samples, which is often prescribed by the pharmaceutical manufacturer because of the ability of the weighing method to be calibrated, is maintained and thus, by means of a comparison between the balance value and the microwave value, the constant k1 is adjusted online.

Figure 2:
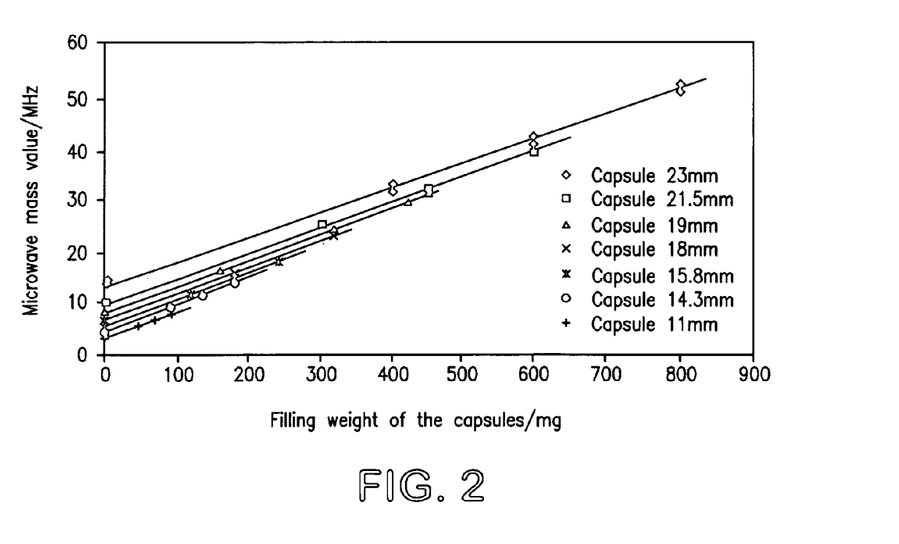
FIG. 2 shows the dependence of the microwave mass value on the weight of the capsules.
Figure 3:
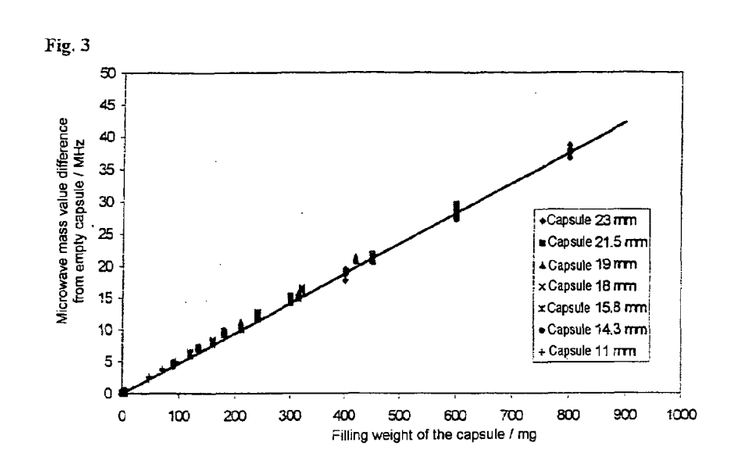
FIG. 3 shows the change in the difference of the mass value measured with microwaves from the corresponding mass value of the empty casings for different capsule weights.

FIG. 2 shows how precisely the microwave mass value represents the different capsule fillings for all the possible capsule sizes between volumes of 23*8.5 mm down to 11*4.5 mm, each capsule sort having been measured 10 times with a defined filling. In this case, the fluctuations of the measured values of the individual capsules can be attributed to the statistical fluctuations of the masses of the empty gelatin capsules. The microwave measured values for the various capsule sizes lie on parallel displaced straight lines, the position being determined by the microwave effect of the empty capsules. This is shown by FIG. 3, in which the changes of the microwave effect with respect to the empty resonator are plotted. The relationship between the change in the microwave mass measured value with respect to that of the empty capsule and the filling mass of the capsule can thus be represented to a good approximation as a single straight line.

Figure 4:
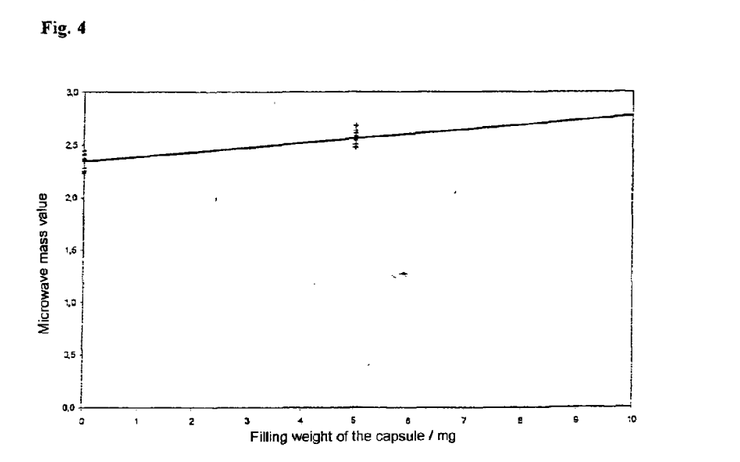
FIG. 4 shows the dependence of the measured mass value on the filling quantity at very small filling quantities.

FIG. 4 shows that, even in the case of extremely small capsule filling quantities of only 5 mg, a distinct rise in the signal as compared with the empty capsules can be seen. However, in a comparison of the scattering width of the microwave measured signals from the empty and the filled capsules, it can be seen that the mass variation within the empty capsules is already of the order of magnitude of the quantity of the filler material to be measured. In this case, in order to achieve adequate measurement precision, either a twofold measurement of the capsule with two microwave resonators is necessary (one before and one after filling) or else pre-sorting of the capsules, so that only capsules with identical mass are employed.

Figure 5:
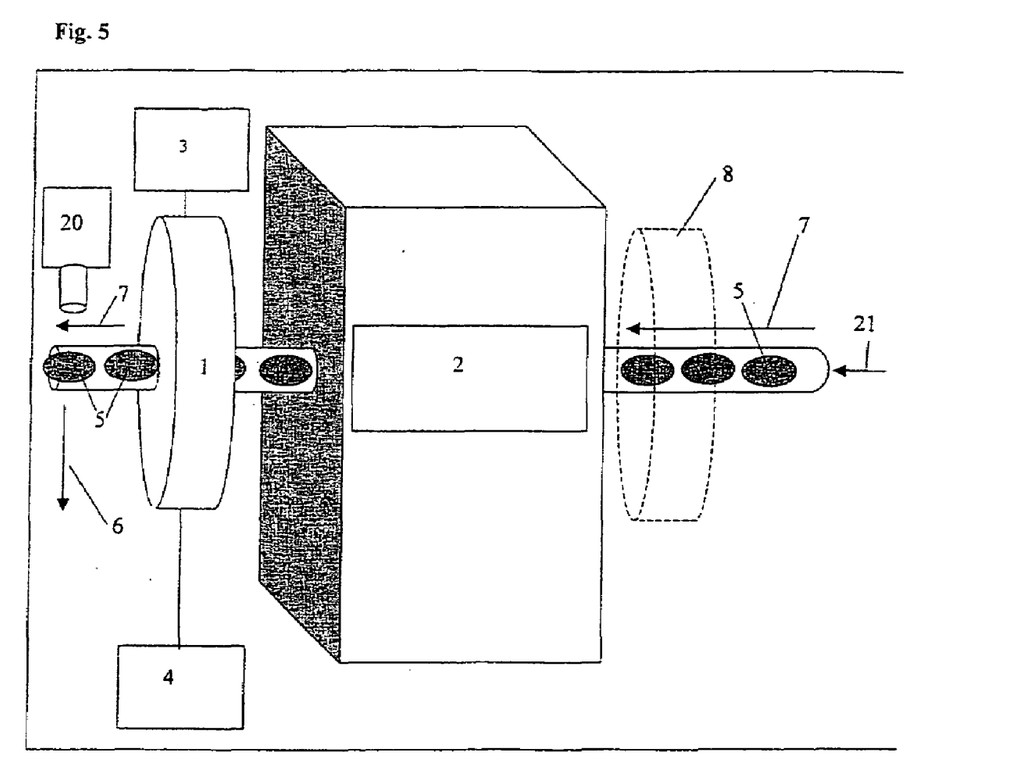
FIG. 5 shows the arrangement of a microwave resonator at the outlet from a machine for producing/filling units of active substances.

FIG. 5 illustrates the arrangement of a microwave resonator 1 at the outlet of a machine for filling capsules. The microwave resonator 1 is fed with microwave energy by a microwave generator, which is illustrated schematically at 3. The microwave energy emerging is then measured by a circuit indicated at 4 and is evaluated by electronics contained therein. If the measurement of a capsule 5 results in its mass not lying within predefined tolerance limits, the corresponding capsule 5 is deflected out of the stream of capsules 5, which normally runs in the direction of the arrow 7, in the direction of the arrow 6 by an ejector device, indicated at 20, with the aid of a puff of air or, for example, in the form of a diverter, the capsules being transported by an air stream which is indicated at 21. By means of appropriate diverters or pulses of air, sorting of the capsules into different containers in accordance with different masses or moistures can also be carried out. In this case, the microwave resonator measuring unit 1, 3, 4 can either be integrated into the machine 2 itself together with the ejection mechanism or else positioned beside the machine 2 as an independent unit which takes the capsules from an intermediate buffer.

In the special case of very small filling masses in capsules 5, in which the range of fluctuation of the empty capsules mass lies in the range of the capsule content, it is expedient to equip a capsule filling system with two microwave resonators. In addition to the microwave resonator 1 at the outlet of the machine 2, a further microwave resonator 8, which is illustrated dashed in FIG. 6, can be provided at the inlet to the machine 2. This is likewise provided with a microwave generator 3 and a measuring and evaluation circuit 4, but these are not shown in FIG. 5. If the control computer of the machine 2 tracks the path of each individual capsule, it can determine the difference between the appropriate full and empty capsule masses and classify the content or sort the capsules.

Figure 6:
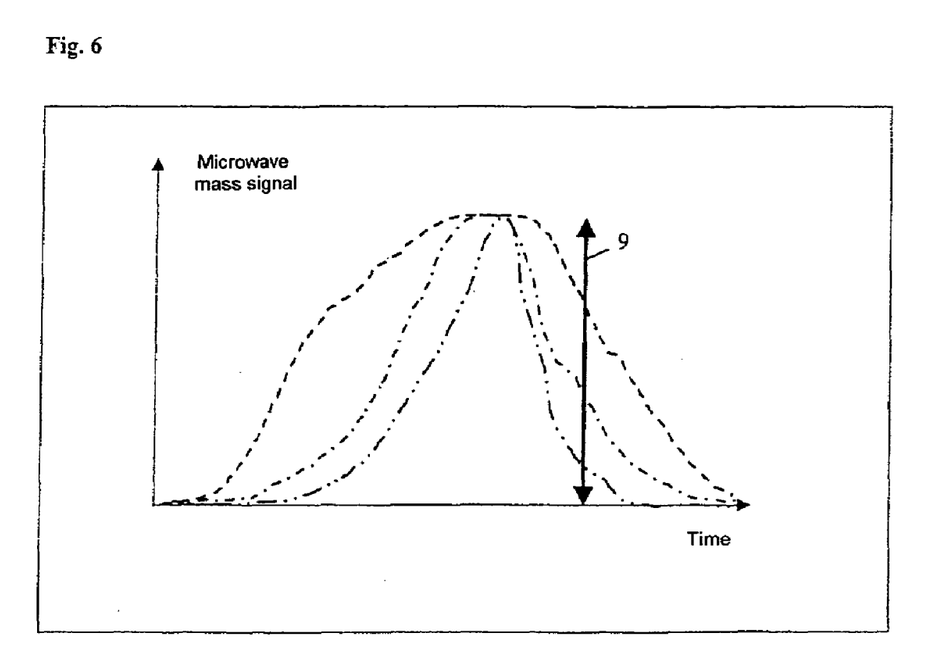
FIG. 6 shows the microwave signal as a unit of active substances passes through the resonator.

The particular requirement on the microwave measuring field for measuring the mass of units of active substances resides in the fact that it must be homogeneous over the entire zone through which the unit of active substances moves and is deterministic of the measured value. Only then is it ensured that the mass-proportional measured signal does not depend on the type of movement and position of the unit of active substances in the measuring field or on the type of distribution of the powder mass within the capsule. In this way, a moving unit of active substances with a specific total mass, irrespective of the type of movement or distribution of the mass within the sample, produces a signal variation over time which, although it depends in detail on the actual type of movement, has an identical maximum value defined by the sample mass. This is because, during the movement of the unit of active substances through the resonator, the mass-proportional values A and B increase and reach a maximum when the entire unit of active substances is located in the electrical measuring field of the resonator. The microwave field, which is constant over the sample, acts like an integration element and produces a maximum value 9 which is unambiguously a measure of the mass of the unit of active substances, as shown in FIG. 6. The three curves in this case show the signals from identical units of active substances which differ because of different movement profiles as they pass through the resonator. However, they have the same maximum value 9, which is a measure of the mass of the unit of active substances.

Figure 7:
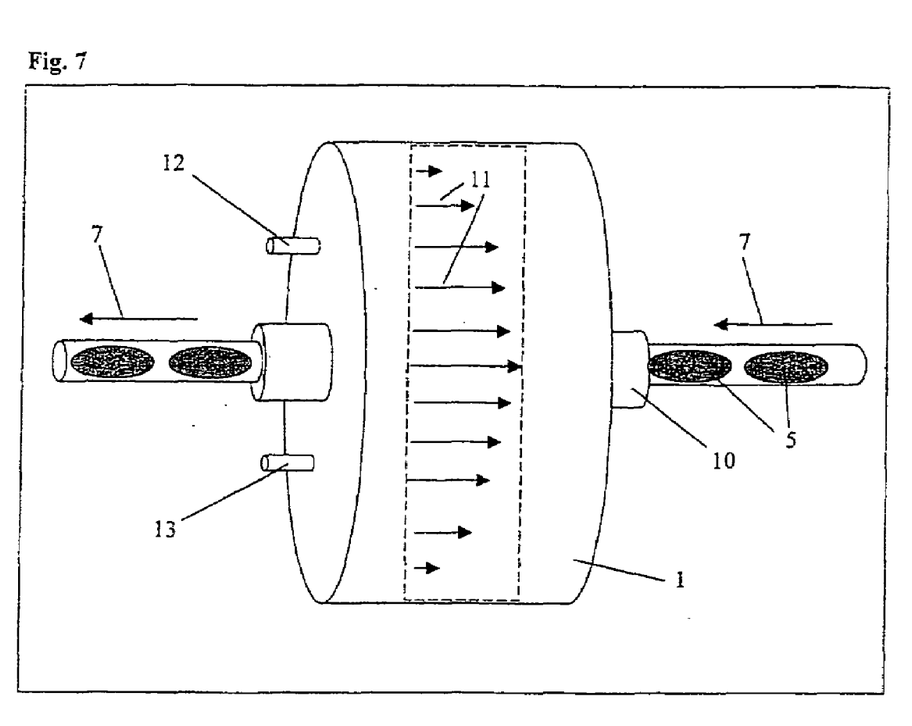
FIG. 7 shows an embodiment of a microwave resonator.

FIG. 7 shows an embodiment of a microwave resonator 1. A resonator 1 in the E010 basic mode is provided with a dielectric sample tube 10 whose internal diameter of 10 mm is somewhat greater than the largest active substance unit diameter to be expected. The electric field strength 11 is constant both in the direction of movement and in the plane perpendicular thereto in the region of the sample tube if the sample is located at the center of the resonator, for which reason this resonator type is very suitable for mass determination in units of active substances, independent of the format, with sample diameters between 9.5 mm and 2 mm. Connections via which the microwaves are coupled into the resonator 1 and out of the same are shown at 12 and 13.

Figure 8:
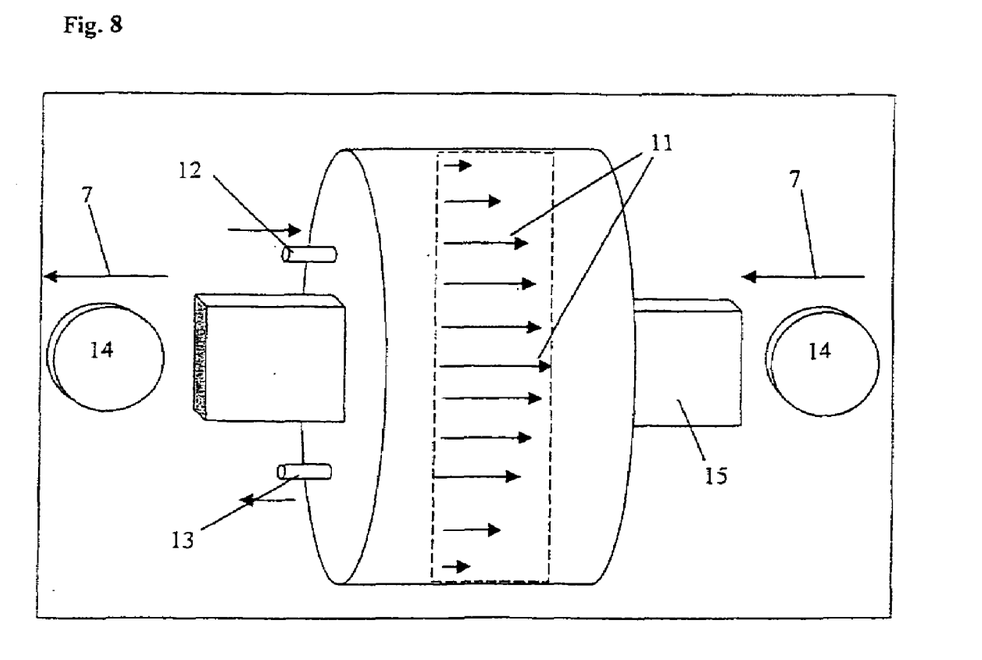
FIG. 8 shows another embodiment of a microwave resonator.

FIG. 8 shows a resonator type for measuring tablets 14 with relatively large diameters (for example lemonade tablets), integration over the entire tablet being possible as a result of the rectangular sample guide 15, if the tablet is located at the center of the resonator. This resonator is also excited in the E010 mode, the slight inhomogeneity in the field line pattern being less significant with very large sample guide dimensions the lower the measuring frequency, that is to say the greater the resonator diameter, is chosen to be. This reduction in the measuring frequency is limited by the measure that, at frequencies below 1 GHz, the losses arising from ion conductivity effects can no longer be neglected as compared with the water dipole losses, and therefore a reliable moisture measurement is no longer possible.

Figure 9:
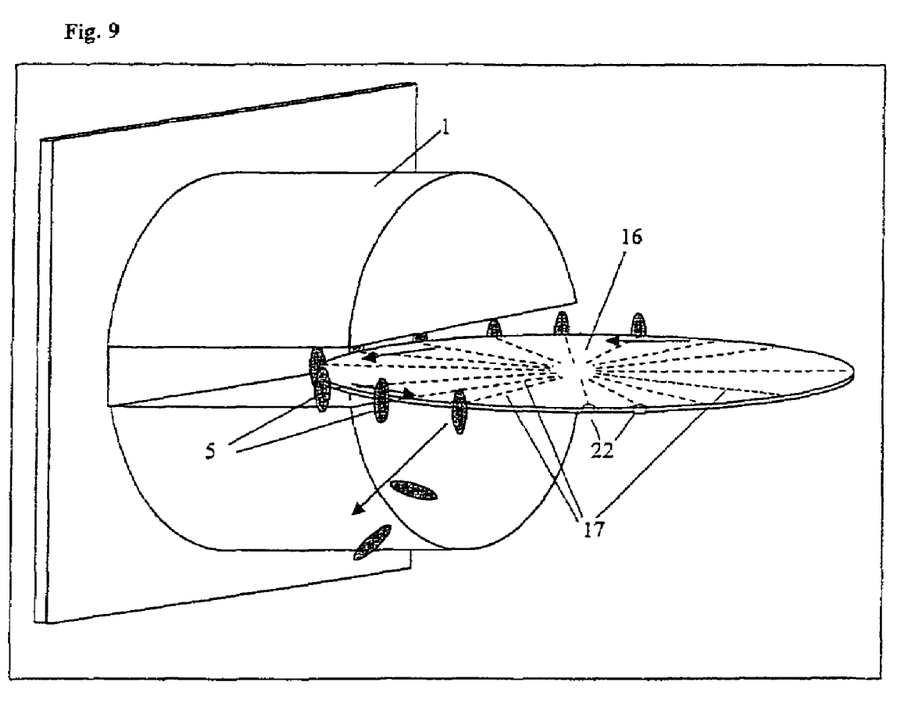
FIG. 9 shows yet another embodiment of a resonator having a different guide for the units of active substances.

FIG. 9 shows a resonator 1 of the type of a fork resonator open on one side, through which the units of active substances can be guided in the upright position, being held in their position via a wheel-like plastic guide 16 and vacuum suction 17. The microwave resonator 1 is in this case excited in an E010 resonance mode known from the cylindrical resonator, the wall surfaces having been divided in such a way that the wall currents are not impaired. If sufficiently thick side walls are provided, so that within this region an exponential field drop toward the outside is possible, this resonator, in spite of large openings, is completely free of emissions and exhibits a very homogeneous measuring field transversely with respect to the direction of movement of the units of active substances. The preconditions for a precise mass and moisture measurement are therefore provided. A further advantage of this arrangement of the resonator is that, at any time, the exact position of the units of active material is known, so that the subsequent treatment and sorting of the units of active substances in accordance with the results of the measurement is easily possible. In order to maintain the exact microwave measured values of the units of active substances, the microwave effects Ao and Bo of the active substance unit guide must previously be measured in the state without a unit of active substances. This can be done, for example, in a separate taring procedure at the start of the actual production process after the machine has been switched on at idle. The actual active substance unit measured values are then given as difference values from the current measured values A and B and the measured values of the active substance unit guide Ao and Bo applicable to the individual positions. If, in the guide wheel, one or more positions are provided at which the microwave effect from the guide wheel without a unit of active substances can be measured on its own (for example the positions designated 22 in FIG. 9), by means of a comparison with the corresponding values from the initial taring, online taring is possible, so that even during non-stop operation over many hours, the effect of temperature changes or resonator contamination can be compensated for automatically without stopping the process. Therefore, precise mass and moisture management is guaranteed even in the event of changes in temperature and contamination of the measuring zone. In the event of a change in the format of the units of active substances, only a replacement of the guide wheel 16 with the suitable skeleton forms 22 for the new units of active substances has to be carried out.

Figure 10:
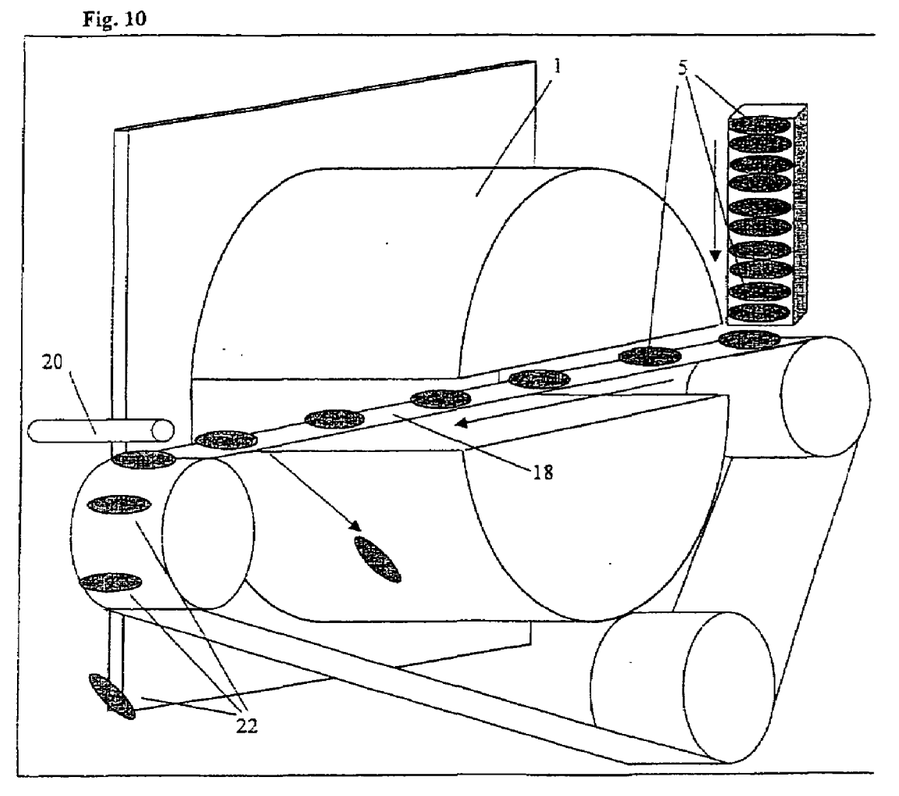
FIG. 10 shows yet another arrangement for measuring the mass of the units of active substances.

FIG. 10 shows a further exemplary embodiment of a unit of active substances 5, a resonator type with a forked resonator 1 open on one side or closed on both sides with a very homogeneous transverse field again being suitable for precise mass and moisture measurement. Since the units of active substances 5 are deposited in depressions 22 on the guide 18, the exact position of the units of active substances is known exactly, so that easy further sorting of the units of active substances is also possible here. As in FIG. 9, the microwave influence of the active substance unit guide 18 must be ensured by initial taring, and its change must be ensured by point-by-point monitoring of the guide online. Here, too, format changes of the units of active substances require replacement of the guide 18, which is designed as an endless belt here, but these can be carried out simply.

The invention claimed is:

1. A method for determining the mass of portioned units of active substances, in particular capsules, tablets or dragees, comprising leading the units of active substances through a microwave field generated by a microwave resonator, determining the mass M of each portioned unit from the displacement A of the resonant frequency and the broadening B of the resonance curve caused by presence of each portioned unit in the microwave field, with compensation for the influence of moisture, by means of a mathematical combination of the two measured variables, which comprises a linear expansion of M with respect to A having first and second coefficients k1, k2, each of the coefficients k1, k2 representing a linear expansion with respect to F, where F=B/A, and sorting the portioned units according to their mass M.

2. The method as claimed in claim 1, wherein the mass is determined with the aid of the relationship $$M=k1*(1+k2*F)*A$$

where k1 and k2 are constants, of which k2 depends on the unit of active substances examined and F=B/A.

3. The method as claimed in claim 2, wherein the moisture is additionally determined.

4. The method for determining the mass of portioned units of active substances as claimed in claim 2, said active substances comprise a casing and the active substance contained therein, wherein the mass of the casing without active substance and then the total mass of the unit of active substances following filling with the active substance are determined.

5. The method as claimed in claim 1, wherein the moisture is additionally determined.

6. The method for determining the mass of portioned units of active substances as claimed in claim 5, said active substances comprise a casing and the active substance contained therein, wherein the mass of the casing without active substance and then the total mass of the unit of active substances following filling with the active substance are determined.

7. The method for determining the mass of portioned units of active substances as claimed in claim 1, said active substances comprise a casing and the active substance contained therein, wherein the mass of the casing without active substance and then the total mass of the unit of active substances following filling with the active substance are determined.

8. The method as claimed in claim 7, wherein the empty casings are sorted by mass and are then filled batchwise and the total mass is determined.

9. The method as claimed in claim 7, wherein the mass of the casing is determined immediately before filling.

10. The method as claimed claim 1, wherein microwaves with frequencies from 1 to 60 GHz, in particular 2 to 30 GHz, are used.

11. An apparatus for determining the mass of portioned units of active substances, in particular capsules, tablets or dragees, which comprises a microwave generator arranged to generate a microwave field in a microwave resonator, a device for guiding the units of active substances through the microwave resonator, measuring and evaluation electronics for determining the mass from the displacement A of the resonant frequency and the broadening B of the resonance curve caused by presence of each portioned unit in the microwave field, and a device for removing individual of the units of active substances having a mass outside a predetermined range, wherein the device for guiding the units of active substances have an endless belt with depressions, into which the units of active substances are inserted.

12. An apparatus for determining the mass of portioned units of active substances, in particular capsules, tablets or dragees, which comprises a microwave generator arranged to generate a microwave field in a microwave resonator, a device for guiding the units of active substances through the microwave resonator, measuring and evaluation electronics for determining the mass from the displacement A of the resonant frequency and the broadening B of the resonance curve caused by presence of each portioned unit in the microwave field, and a device for removing individual of the units of active substances having a mass outside a predetermined range, wherein the device for guiding units of active substances have a circular disk, on the circumference of which the units of active substances are held firmly with the aid of vacuum.

* * * * *

UNITED STATES PATENT AND TRADEMARK OFFICE
CERTIFICATE OF CORRECTION

PATENT NO.        : 7,337,074 B2                                    Page 1 of 1
APPLICATION NO.   : 10/820244
DATED             : February 26, 2008
INVENTOR(S)       : Herrmann et al.

It is certified that error appears in the above-identified patent and that said Letters Patent is hereby corrected as shown below:

<u>Title page,</u>

Item "( * ) Notice:"  insert

Item --(73) Assignee:    TEWS Electronik Dipl.Ing. Manfred Tews,
                         Hamburg, Germany (DE)--

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,337,074 B2
APPLICATION NO. : 10/820244
DATED : February 26, 2008
INVENTOR(S) : Herrmann et al.

It is certified that error appears in the above-identified patent and that said Letters Patent is hereby corrected as shown below:

<u>Title page,</u>

Item "( * ) Notice:" insert

Item --(73) Assignee:   TEWS Elektronik Dipl.Ing. Manfred Tews, Hamburg, Germany (DE)--

This certificate supersedes the Certificate of Correction issued June 10, 2008.

Signed and Sealed this

Twenty-ninth Day of July, 2008

JON W. DUDAS
*Director of the United States Patent and Trademark Office*